United States Patent [19]
Zumalt et al.

[11] 3,979,182
[45] Sept. 7, 1976

[54] CHEMICAL DETECTION OF NITROGEN CONTAINING COMPOUNDS

[75] Inventors: Michael D. Zumalt, Sacramento, Calif.; Neil R. Hofmann, Angola, N.Y.; Melvin C. Bassett, Baltimore, Md.

[73] Assignee: The United States of America as represented by the Secretary of the Army, Washington, D.C.

[22] Filed: Apr. 29, 1969

[21] Appl. No.: 821,168

[52] U.S. Cl. .......................... 23/232 R; 23/254 R; 252/408
[51] Int. Cl.² .......................................... G01N 27/62
[58] Field of Search ............ 23/253, 254, 256, 230, 23/232, 230 R, 232 R; 260/944, 961; 252/408; 117/1.7; 73/40.7

[56] References Cited
UNITED STATES PATENTS 3,172,902  3/1965  Szabo et al. ...................... 260/461
3,253,061  5/1966  Schlor et al. ...................... 260/954

Primary Examiner—Verlin R. Pendegrass
Assistant Examiner—Peter A. Nelson
Attorney, Agent, or Firm—Nathan Edelberg; Kenneth P. Van Wyck

[57] ABSTRACT

A stable detector composition comprising a lower alkyl alcohol, a dialkyl ketone, a nitrobenzene and collodion for compounds having the formula

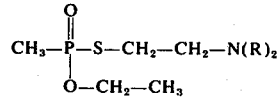

wherein R is ethyl or isopropyl and their decomposition products.

7 Claims, No Drawings

CHEMICAL DETECTION OF NITROGEN CONTAINING COMPOUNDS

DEDICATORY CLAUSE

The invention described herein may be manufactured, used, and licensed by or for the Government for governmental purposes without the payment to us of any royalty thereon.

This invention relates to a novel detecting system for toxic materials.

The object of this invention is the chemical detection of nitrogen containing toxic compounds.

A further object of the invention is the detection of vapor or liquid state of the toxic materials.

The present invention comprises a novel anhydrous detecting composition including 50 ml lower alkyl alcohol, 10 ml dialkyl ketone, 0.62 to 6.20 g. nitrobenzene, and 50 to 100 ml collodion (solution of nitrated cellulose in ether and alcohol). The solution is applied as a coating upon a suitable supporting substrate. Colorless detector coating composition turns a variable color whose pigment or dye resembles, for example, red, maroon, cardinal, or ruby, upon contact with the liquid or vapor phase of the toxic material.

The sensitivity of the system is that the toxic material in quantities from 1 to more than 1000 parts per million can be easily detected.

The single known method to detect the toxic agents in the vapor phase of the formula

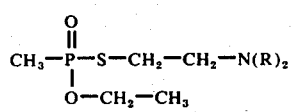

wherein R is ethyl or isopropyl is non chemical and requires the use of animals in order to indicate presence of the agents. The animal, rabbit or pigeon, is placed in the area where the toxic agents are suspected and upon death of the animal the agent was considered to be present. The use of animals for this purpose is not only unsatisfactory but also very limiting.

Our investigation was based upon the inability of the military forces to detect by chemical means the toxic quantities of nitrogen containing compounds in their vapor state. A result of our work is the first chemical detector of great sensitivity, stability as to temperature, storage time, and visual indication of micro-quantities of the toxic material.

There is danger involved in handling toxic material. The hazards are increased by the large number of control points and handling operations the toxic materials must pass through, i.e. manufacture, storing, and transportation to the area of use.

An advantage of our system resides that during various shipping and storing steps leakage of the toxic material can be ascertained without opening the shipping containers. A small sealed, clear, window is made in the transportation container with the inventor's detector visible through the window. Any escape of the toxic material especially in its vapor state from its container can be seen without the need of breaking the seal of the shipping container for leak testing, thus without further endangering the atmosphere with the toxic material.

The toxic compounds of the formula

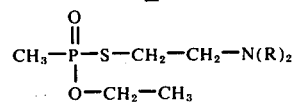

wherein R is ethyl or isopropyl and their method of preparation, set forth in Example 1, were the result of classified research and do not form part of the inventive portion of this invention.

EXAMPLE 1 a. The method of producing O-ethyl S-diethylaminoethyl methylphosphonothiolate the steps comprising to a 50.0 ml of 0.4 M sodium hydroxide solution was added to 100 ml aqueous solution containing 9.17 g (0.04 moles) potassium ethyl methylphosphonothiolate, and then adding 200 ml of an aqueous solution containing 3.44 g (0.02 moles) of beta-chloroethyl diethylamine hydrochloride. The solutions were mixed and allowed to stand for five minutes. The pH of the solution was between 10.0 and 10.5. After five minutes, 50 ml of 0.04 M acetic acid was added. The pH dropped to 5.15. The solution pH was adjusted and maintained at 10.5 and extracted with diethyl ether. The extract was dried over anhydrous sodium sulfate and distilled yielding O-ethyl S-diethylaminoethyl methylphosphonothiolate.

b. Potassium ethyl methylphosphonothiolate is dissolved in water and the pH of the solution is adjusted to 10 by the addition of concentrated sodium hydroxide. An aqueous solution of beta-chloroethyl diisopropylamine at pH 10 is added. The mixture is then treated in the same manner as (a) supra, and recovering O-ethyl S-diisopropylaminoethyl methylphosphonothiolate.

We also found that the breakdown products of the toxic agents from Example 1 can be demonstrated by the detecting system of this invention. Accordingly, it is a means for indicating the loss of potency of the toxic agents.

One of the unexpected results of our findings was the insensitivity to temperature in view of the fact that our method is operative between −4°F and 165°F. The system of this invention gave immediate and positive results after storage of 8 weeks or longer under desert, tropic or artic conditions. This is a detector which the military forces can use in the field for self-protection in combat zones since one system is operative in the various theaters of operations.

EXAMPLE 2 a. The method of preparing the detector composition comprises the sequence of steps adding 50 ml ethyl alcohol to 10 ml acetone with subsequent mixing then adding 2.0 g. 1,3,5-trinitrobenzene, and final addition of 100 ml of collodion. There is sufficient mixing of the components after addition in order that they are either dissolved or miscible.

b. Other detecting solutions made in accordance with (a) above, are set forth in Table I.

Table I

| | | | | | | | | |
|---|---|---|---|---|---|---|---|---|
| Ethyl Alcohol ml | 50 | 50 | 50 | 50 | 50 | 50 | 50 | 50 |
| Acetone ml | 10 | 10 | 10 | 10 | 10 | 10 | 10 | 10 |
| Nitrobenzene grams | 3.0 | 1.25 | 1.50 | 3.0 | 1.75 | 0.62 | 2.0 | 6.20 |
| Collodion ml | 50 | 50 | 75 | 100 | 100 | 100 | 100 | 100 |

1,3,5-trinitrobenzene.

EXAMPLE 3 a. The detecting composition, Example 2(a), was coated on a glass rod and inserted into the vapor phase of 1000 part per million of liquid agent, O-ethyl S-diisopropylaminoethyl methylphosphonothiolate, contained in a closed chamber and gave rise to a red color coating, positive test, within one hour at room temperature.

b. The procedure and composition in (a) supra, was repeated with the substitution of 3 parts per million of the agent and gave rise to a positive test within 8 hours at room temperature.

c. Utilizing the detector coating, procedure and agent of (a) above, a series of experiments under various temperatures and storage times are summarized below.

| Temp. (0 F) | Detector on Glass Rod Storage Time, Weeks | Concentration of Agent Parts per million | Result (0°F) at room temperature unless indicated |
|---|---|---|---|
| Artic (−60°) | 2 | 100 | + |
| | 6 | 10 | + (−4°) |
| | 10 | 100 | + |
| | 10 | 1 | + |
| Desert (+160°) | 2 | 100 | + |
| | 6 | 10 | + (+160°) |
| | 10 | 100 | + |
| | 10 | 1 | + |
| Tropic (+113° and 85% Relative Humidity) | 2 | 100 | + |
| | 6 | 10 | + (113° and 85% Relative Humidity) |
| | 10 | 100 | + |
| | 10 | 1 | + |

There appears to be no upper limit of the proportion of toxic agent that can be detected by our system but we did not go beyond the amount of 1000 parts per million.

EXAMPLE 4

A detecting solution, Example 2, was applied to a suitable flat self-supporting substrate. The method is a conventional double-dipping procedure comprising the steps for the first coating by inserting the substrate into and then removing from said solution avoiding the formation of bubbles with complete drying in about 2 hours. The second coating and drying steps were carried out in the same manner as the first coating procedure. The coated substrate does not require any special handling for storing, that is, in a slide box, and is operative for about four months. Although no special conditions are required for the coating process, the optimum results may be obtained by the procedure in a temperature range between 60° to 75°F avoiding bubble formation and humidity below 50%. No special cleaning of the substrate is required other than free from lint.

The supporting substrate is any inert material not affected by the coating such as glass.

We claim:

1. In a method for detecting toxic compounds the step comprising contacting an effective amount of compounds of the formula

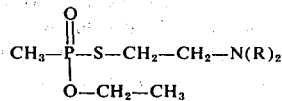

wherein R is ethyl or isopropyl and their decomposition products with a composition comprising a lower alkyl alcohol, a dialkyl ketone, a nitrobenzene and collodion.

2. A method according to claim 1, wherein the composition comprises 50 ml alcohol, 10 ml ketone, 0.62 to 6.20 g nitrobenzene and 50 to 100 ml collodion.

3. A method according to claim 1, wherein the compounds are in liquid or vapor phase.

4. A method according to claim 1, wherein the composition is a colorless film.

5. A method according to claim 1, wherein the composition is supported on an inert substrate.

6. a method according to claim 1, wherein the composition comprises 50 ml ethyl alcohol, 10 ml dimethyl ketone, 0.62 to 6.20 g 1,3,5-trinitrobenzene and 50 to 100 ml collodion.

7. A method according to claim 1, wherein contacting the compounds of the formula and their decomposition products with the composition produce a reddish color.

* * * * *